United States Patent [19]

Trelles et al.

[11] Patent Number: 5,578,029
[45] Date of Patent: Nov. 26, 1996

[54] METHOD OF TREATING VEINS

[75] Inventors: Mario A. Trelles, Cambrils, Spain;
Dale F. Koop, Sunnyvale, Calif.

[73] Assignee: Coherent, Inc., Santa Clara, Calif.

[21] Appl. No.: 598,657

[22] Filed: Feb. 8, 1996

Related U.S. Application Data

[62] Division of Ser. No. 311,509, Sep. 23, 1994, Pat. No. 5,531,739.

[51] Int. Cl.$^6$ .................................................. A61B 17/36
[52] U.S. Cl. ................................. 606/25; 606/9; 606/15
[58] Field of Search ............................ 606/4, 5, 6, 7, 606/9, 10, 11, 12, 14, 15, 16, 17

[56] References Cited

U.S. PATENT DOCUMENTS

| | | | |
|---|---|---|---|
| 5,000,752 | 3/1991 | Hoskin et al. | 606/9 |
| 5,025,446 | 6/1991 | Kuizenga | 372/21 |
| 5,217,455 | 6/1993 | Tan | 606/9 |
| 5,282,797 | 2/1994 | Chess | 606/9 |
| 5,282,798 | 2/1994 | Bruse et al. | 606/4 |
| 5,287,380 | 2/1994 | Hsia | 372/69 |
| 5,290,273 | 3/1994 | Tan | 606/9 |
| 5,304,170 | 4/1994 | Green | 606/9 |
| 5,312,395 | 5/1994 | Tan et al. | 606/9 |
| 5,312,396 | 5/1994 | Feld et al. | 606/11 |
| 5,431,646 | 7/1995 | Vassiliadis et al. | 606/6 |
| 5,476,461 | 12/1995 | Cho et al. | 606/17 |

FOREIGN PATENT DOCUMENTS

| | | |
|---|---|---|
| WO90/12545 | 11/1990 | WIPO . |
| WO91/13652 | 9/1991 | WIPO . |

*Primary Examiner*—Angela D. Sykes
*Assistant Examiner*—Sonya Harris-Ogugua
*Attorney, Agent, or Firm*—Limbach & Limbach L.L.P.

[57] ABSTRACT

A method is disclosed for treating veins. In the subject method, the skin is pierced with the sharpened tip of a fiber optic probe. The probe is advanced to a location underneath the vessel to be treated. Once in position, the vessel is irradiated with a treatment beam having a fluence sufficient to coagulate and collapse the vessel at that location. The procedure is then repeated at multiple sites along the length of the vessel so that it will collapse along its length and no longer carry any blood. In the preferred embodiment, a curved probe is used to facilitate the insertion of the tip under the vessel.

2 Claims, 1 Drawing Sheet

METHOD OF TREATING VEINS

This is a divisional of application Ser. No. 0/311,509, filed Sep. 23, 1994 Pat. No. 5,531,739, issued Jul. 2, 1996.

TECHNICAL FIELD

The subject invention relates to an improved method for the laser treatment of veins.

BACKGROUND OF THE INVENTION

There has been significant interest in developing laser systems which can be used to treat various forms of vascular lesions. The type of vascular disorders that have been investigated include port wine stains, face veins, telangiectasis, and birth marks. A wide variety of medical laser systems have been proposed and introduced to treat these various disorders. In most prior systems, the laser is used to irradiate the surface of the skin. The laser energy penetrates through the skin and is absorbed in the blood, which coagulates and collapses the vein.

Many of these prior art laser systems have shown promise, particularly when used to treat small, surface veins. However, significant problems have been encountered when these systems are used to treat deeper veins, most commonly found on the lower extremities. More specifically, in order to treat deeper veins, relatively high laser powers are necessary. When using these high powers, surface scarring can occur as well as significant changes in skin coloration.

Due to the problems outlined above, deeper veins are most often treated surgically, by cutting the skin and physically tying off the vein. This approach is often used in conjunction with injecting the vein with an agent which essentially poisons the cells, in a procedure known as sclerotherapy. Unfortunately, these surgical approaches also have problems including pain, pigmentation and telangiectatic matting.

Accordingly, it would be desirable to develop an alternative method for treating veins which does not have the drawbacks associated with the prior art approaches.

SUMMARY OF THE INVENTION

In accordance with the method of the subject invention, the veins are directly treated with laser energy. To achieve this goal, a fiber optic probe is provided having a sharpened, needle-like point which can be used to pierce the skin of the patient. The probe is then advanced towards the vein. Preferably, the probe is side firing and the tip is advanced to a location under the vein. A visible aiming beam can be used to highlight the location of the vein.

Once the tip of the probe is aligned with the vein, it is irradiated with laser radiation in order to coagulate the vessel. This procedure is repeated at multiple sites along the vein in a manner to cause the vein to collapse.

Since the probe is adjacent the vein, much less fluence is required to coagulate the vessel. This results in reduced thermal damage and scarring.

Further objects and advantages of the subject invention will become apparent from the following detailed description taken in conjunction with the drawings in which:

DETAILED DESCRIPTION OF THE PREFERRED EMBODIMENT

Figure 1:
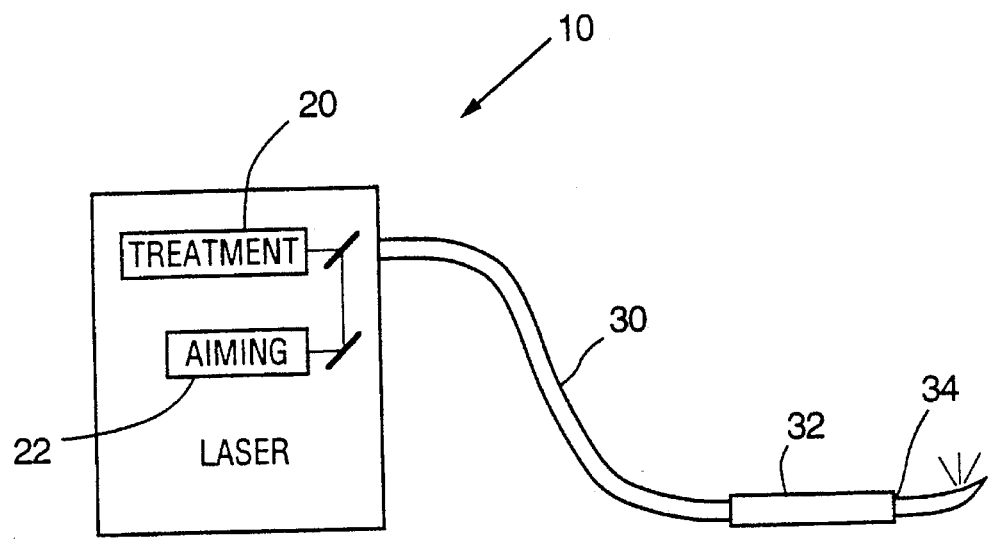
FIG. 1 illustrates a laser system and probe for use in the method of the subject invention.

Referring to FIG. 1, there is illustrated a laser system 10 for performing the method of the subject invention. The laser system includes a treatment laser 20 generating an output beam. In initial experiments, the treatment laser was defined by an argon ion laser. It is envisioned that other treatment lasers, such as krypton lasers and argon pumped dye lasers, could be used. In addition, various solid state lasers may be useful. Such solid state lasers include Nd:YAG (in both Q-switched and frequency doubled variations), Ho:YAG and Er:YAG.

The predominant output of an argon ion laser is at 514 nm. This wavelength is green and, at low power levels, can be used as an aiming beam since it can be easily visualized in blood. As an alternative, the aiming beam can be generated by a separate laser 22. In this case, the visible aiming beam is delivered colinearly with the treatment beam.

One argon laser which has been found suitable for the treatment of vessels in accordance with the subject procedure is manufactured by Coherent, Inc. and sold under the model designation "970". This laser is capable of generating a few watts of power, all lines The output from the argon laser is delivered via a fiber optic cable 30. The fiber optic cable terminates in a probe 32. Similar fiber optic cables and probes have been available in the prior art for various ophthalmic procedures using an argon laser.

In order to operate with the subject method, the prior art probe should be modified to enable the probe to pierce the skin. To achieve this goal, the outer tubular member 34 of the probe should be formed from surgical steel. The tip 36 should be sharpened to a needle point. The diameter of the probe should be relatively small to minimize pain. It is believed that the diameter of the probe should be 1 mm or less.

Mounted within the probe is an optical fiber selected to transmit the laser beam. The diameter of the internal fiber would typically be on the order of 200 to 600 microns and preferably 400 microns.

In the preferred embodiment, a side firing probe is used. In a side firing probe, light is emitted transverse to the longitudinal axis of the fiber. One method for achieving this goal is to position an angled reflector beyond the delivery end of the fiber. Another approach is to form an angle on the end of the fiber and rely on total internal reflection within the fiber. In the illustrated embodiment, the probe tip is curved in a manner to emit the treatment beam transverse to the longitudinal axis of the fiber. In any case of side firing probes, it is desirable to include a marker on the handpiece to illustrate the propagation direction of the laser beam.

Figure 2:
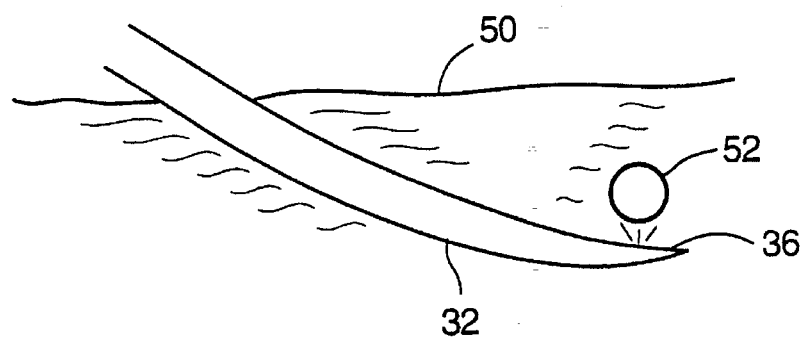
FIG. 2 is a sectional view illustrating the probe inserted into a position to treat a blood vessel.

FIG. 2 illustrates the preferred procedure for treating the vein. The sharpened tip 36 of the probe 32 is used to pierce the skin 50 at a point about a centimeter away from the vein 52 to be treated. The probe is then advanced forward and downwardly so that the tip 36 is beneath the vein and as close to the outer surface of the vein as possible.

As the probe is advanced, the visible aiming beam should be active. In practice, the aiming beam diffusely illuminates the region to be treated. When the tip is positioned under the vein, the shadow of the vein is clearly visible and proper positioning is facilitated.

Once the probe tip is in the proper position, the treatment beam is activated. In initial experiments with a three watt argon laser system, a pulsed output was used, where the pulses were on the order of 200 to 500 milliseconds. If a higher power laser is available, the pulse length can be reduced. The energy of the treatment beam is absorbed in the hemoglobin of the blood. This absorption causes rapid heating, resulting in coagulation and necrosis of the vein in a narrow region. The coagulation and necrosis causes the vein to collapse at that location.

The use of the aiming beam allows the physician to visualize the collapse of the vein. In practice, multiple pulses are required. Usually, four pulses are sufficient to collapse a vein having a diameter between 200 to 600 microns.

Once the probe tip has been inserted under the skin, the vein can be treated at multiple sites without removing the probe. In practice the tip of the probe can be moved about under the skin over a four by four square centimeter region.

Figure 3:
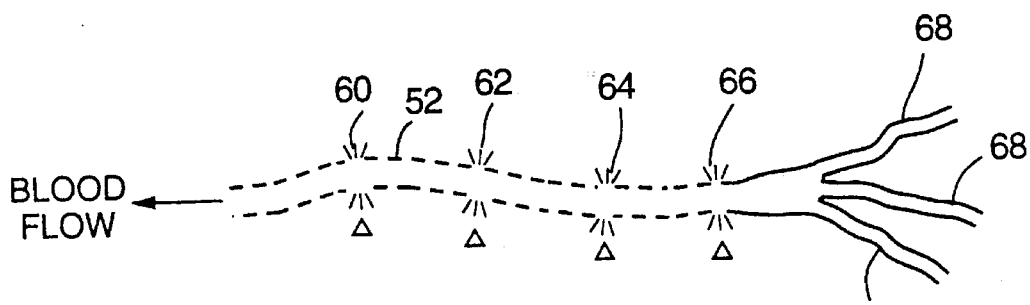
FIG. 3 is a top view illustrating a pattern of sites used to treat a vessel.

In order to collapse a long length of the vein, the skin must be punctured at a number of sites. As seen in FIG. 3, it is desirable to locate the first treatment site 60 at a downstream point with respect to the flow of blood in the vessel. The surgeon can then sequentially treat the vessel at multiple sites (62, 64, 66) upstream from the first site 60. In initial experiments, the spacing between the sites was between 1 and 5 cm.

The reason for beginning treatment of the vein at a downstream point with respect to the blood flow is twofold. First, in order to get the best long term results, it is necessary to treat each vein at multiple sites. If an upstream point in the vein is treated first, the downstream section of the vein will immediately collapse making finding and treating additional downstream sections of the vein more difficult. Secondly, if the larger downstream sections of the vein are treated first, the need to treat the smaller upstream tributary branches 68 can be reduced.

Although the subject method requires invasion of the skin, it does have some significant advantages when compared to prior laser treatment systems where only the surface of the skin is irradiated. For example, since the laser energy is directed only into the vein, much lower fluence levels are required to achieve the desired result. Since much lower fluence levels are used, the amount of thermal damage to adjacent regions is substantially lessened. In addition, since the skin is not irradiated, the chances of scarring and coloration changes are minimized.

In practice, thermal damage to the skin can be further minimized by cooling the skin surface during treatment. This result can be achieved by spraying the skin with known surface coolants, such as chloroethelyne, which is typically used by athletes after an injury.

While the subject invention has been described with reference to a preferred embodiment, various changes and modifications could be made therein, by one skilled in the art, without varying from the scope and spirit of the subject invention as defined by the appended claims.

We claim:

1. A fiber optic probe for use in treating blood vessels under the skin comprising:

a hollow tubular member having a sharpened needle-shaped tip configured for piercing the skin thereby permitting the tubular member to be advanced along side of a blood vessel located under the skin; and an optical fiber supported within the tubular member, said optical fiber for transmitting laser radiation from an input end to a delivery end and wherein the delivery end terminates within the tubular member, said delivery end being configured to direct most of the laser radiation emitted therefrom along an axis transverse to said tubular member and towards said vessel.

2. A fiber optic probe as recited in claim 1 wherein the end of said tubular member is curved.

* * * * *